United States Patent [19]

Aspnes

[11] Patent Number: 5,277,747
[45] Date of Patent: Jan. 11, 1994

[54] EXTRACTION OF SPATIALLY VARYING DIELECTRIC FUNCTION FROM ELLIPSOMETRIC DATA

[75] Inventor: David E. Aspnes, Watchung

[73] Assignee: Bell Communications Research, Inc., Livingston, N.J.

[21] Appl. No.: 945,086

[22] Filed: Sep. 15, 1992

[51] Int. Cl.$^5$ .............................................. G01J 4/00
[52] U.S. Cl. ........................................ 156/626; 437/8; 427/8; 118/712; 356/369; 204/192.13; 204/192.33; 204/298.03; 204/298.32
[58] Field of Search .................... 156/626, 627; 437/8; 427/8-10; 118/712; 356/369; 204/192.13, 192.33, 298.03, 298.32

[56] References Cited

U.S. PATENT DOCUMENTS

| | | | |
|---|---|---|---|
| 4,332,833 | 6/1982 | Aspnes et al. | 156/626 X |
| 4,676,644 | 6/1987 | Canteloup | 156/626 X |
| 5,091,320 | 2/1992 | Aspnes et al. | 437/8 |
| 5,131,752 | 7/1992 | Yu et al. | 156/626 X |

OTHER PUBLICATIONS

D. E. Aspnes et al., "Optical control of growth of $Al_xGa_{1-x}As$ by organometallic molecular beam epitaxy," Applied Physics Letters, 1990, vol. 57, pp. 2707-2709.
D. E. Aspnes et al., "Growth of $Al_xGa_{1-x}As$ parabolic quantum wells by real-time feedback control of composition," Applied Physics Letters, 1992, vol. 60, pp. 1244-1246.
D. E. Aspnes, "Optical Properties of Solids: New Developments," Spectroscopic Ellipsometry of Solids, 1976, B. O. Seraphin (ed.), North Holland, Amsterdam, p. 829.

Primary Examiner—Thi Dang
Attorney, Agent, or Firm—Leonard C. Suchyta

[57] ABSTRACT

A method of and apparatus for extracting dielectric constants from ellipsometric data taken during the growth of a semiconductor thin film and using the extracted dielectric constants to control the composition of the growing film by adjusting the growth conditions. An expression is used for the derivative of the pseudo-dielectric function with respect to the thickness of the thin film within a three-phase model, and the expression is exact to first order in thickness of the film. The expression is quadratic with respect to the dielectric function for a homogeneous thin film and additionally depends on the dielectric function of homogeneous substrate underlying the thin film. Values of the measured pseudo-dielectric function are substituted for the dielectric function of the substrate, and the expression is then solved for the dielectric function of the thin film.

11 Claims, 1 Drawing Sheet

EXTRACTION OF SPATIALLY VARYING DIELECTRIC FUNCTION FROM ELLIPSOMETRIC DATA

FIELD OF THE INVENTION

The invention relates generally to optical measurement techniques. In particular, the invention relates to the control by ellipsometry of parameters of thin-film growth.

BACKGROUND ART

In U.S. Pat. No. 5,091,320, Aspnes et al. described a method for real-time control of the growth of thin films of compound semiconductors by use of ellipsometry. This patent is incorporated herein by reference, and the same work was reported by Aspnes et al. in "Optical control of growth of $Al_xGa_{1-x}As$ by organometallic molecular beam epitaxy," *Applied Physics Letters*, volume 57, 1990, pp.2707-2709 and in "Growth of $Al_x$-$Ga_{1-x}As$ parabolic quantum wells by real-time feedback control of composition," ibid., volume 60, pp. 1244-1246. Quinn has disclosed a method of aligning the ellipsometer in U.S. patent application, Ser. No. 07/723,580, filed Jul. 1, 1991. The general operation of the ellipsometric feedback control of thin-film growth is illustrated in FIG. 1. A thin film 10 of AlGaAs is grown on a GaAs substrate 12 by organo-metallic molecular beam epitaxy (OMMBE) performed within a growth chamber 14 pumped to low pressures by a pump 16. Arsine ($AsH_3$) is supplied to a cracking unit 18 where it is cracked into molecular arsenic ($As_2$) which irradiates the heated substrate 12 on which the thin film 10 is growing. Gas-entrained triethylgallium and triethylaluminum or triisobutylaluminum are supplied to ports 20 and 22. The respective gases irradiate the hot thin film 10, upon the hot surface of which the triethylgallium and the triethylaluminum crack into gallium and aluminum. The arsenic, gallium, and aluminum then chemically combine to epitaxially form the thin film 10 with the crystalline orientation of the substrate. The amounts of the three constituents are controlled by respective valves 24, 26, and 28. The chamber 14 is maintained with an overpressure of arsenic so that the alloying fraction x for $Al_xGa_{1-x}As$ is determined by the relative amounts of triethylgallium and triethylaluminum.

An ellipsometer continuously monitors the thin film 10 while it is being grown. In the ellipsometer, an incident beam of light 30 from a wide-band light source 32 has its linear polarization angle continually changed by a rotating Rochon prism 34. A beam 36 reflected from the thin film 10 is focused in a monochromator 38 through a fixed analyzer prism, and the intensity of its monochromatic output is detected by a photomultiplier tube 40. A computer system 42 receives the intensity of the monochromatic light for multiple sampling periods during at least one complete rotation of the polarizer 34 and uses this data to calculate the ellipsometric parameters $\psi$ and $\Delta$. It thus establishes the complex reflectance ratio $$\rho = \tan\psi e^{i\Delta} = r_p/r_s, \qquad (1)$$

where $r_p$ and $r_s$ are the complex reflectances for p- and s-polarized light, respectively. The complex reflectance coefficients are ratios of complex field coefficients for different polarizations and are not themselves measured.

Aspnes et al. rely on the fact that the ellipsometrically measured parameters can be related through the complex reflectance ratio $\rho$ to the composition of the thin film 10 to compare the ellipsometrically determined composition to the target composition and to accordingly adjust the Al valve 28 in real time so as to correct the composition being deposited. Their formalism relies on the fact that the complex reflectances themselves, and therefore their ratio, can be related within some simple models to material properties, such as material composition or the dielectric constant $\epsilon$, which is directly related to the composition. That is, they use ellipsometry to continuously physically characterize the deposited film and to readjust in real time the growth conditions to thereby achieve a film of the desired characteristic. In particular, they assume a three-phase model consisting of a homogeneous substrate having a dielectric constant $\epsilon_s$, a homogeneous thin film having a dielectric constant $\epsilon_o$, and a homogeneous ambient having a dielectric constant $\epsilon_a$, which in the case of air or vacuum is equal to one. Closed-form solutions exist within the three-phase model for the complex reflectances $r_p$ and $r_s$ in terms of the complex dielectric function $\epsilon_o$ of the film and its thickness t. They then expand this closed-form to first order in t and observe that, as the film thickness t increases, both complex reflectances follow a spiral $$Z = e^{j2k_o t} \qquad (2)$$

in the complex plane. The locus spirals inwardly from the complex reflectance $r_{sa}$ for the bare substrate to the complex reflectance $r_{o\alpha}$ for an optically thick film. In this equation, $$k_o = \frac{\omega}{c}(\epsilon_o - \epsilon_a\sin^2\phi)^{\frac{1}{2}}, \qquad (3)$$

where $\phi$ is the angle from the normal for both the incident and reflected beams, $\omega$ is the frequency of the light, and c is the speed of light. Specifically, closed-form equations exist in this model for both $r_p$ and for $r_s$, both of the form $$r = r_{o\alpha} + [r_{sa} - r_{o\alpha}]e^{j2k_o t}. \qquad (4)$$

In these equations, the material information of the homogeneous film is contained in $k_o$ and $r_{o\alpha}$. Because ellipsometric measurements do not permit $r_s$ and $r_p$ to be individually determined, Aspnes et al. work with the complex reflectance ratio which is approximated by $$\rho \approx \rho_{o\alpha} + [\rho_{sa} - \rho_{o\alpha}]e^{j2k_o t}. \qquad (5)$$

However, the form of Equation (5) is accurate only to the extent that $$|(r_{sa}^2 - r_{o\alpha}^2)e^{j2k_o t}| << |r_{o\alpha}^2|. \qquad (6)$$

In fact, they work within the formalism of the pseudo-dielectric function $<\epsilon>$ which is the complex dielectric constant seen by an ellipsometer. That is, it assumes a two-phase model of a homogeneous sample for which material parameters can be analytically related to ellipsometric data, for example, $$\langle\epsilon\rangle = \sin^2\phi + \sin^2\phi\tan^2\phi\left[\frac{1-\rho}{1+\rho}\right]^2, \quad (7)$$

where $\langle\epsilon\rangle$ would be the uniform dielectric constant of the homogeneous sample. They then assume that the complex pseudo-dielectric function $\langle\epsilon(t)\rangle$ will follow the same complex spiral as a function of the thickness of a uniform film $$\langle\epsilon(t)\rangle = \epsilon_o + (\epsilon_s - \epsilon_o)e^{j2k_o t}. \quad (8)$$

In essence, this is equivalent to performing another first-order expansion, this one performed on Equation (7). Therefore, as the film thickness t increases from zero to a large value, an ellipsometrically measured complex dielectric function will follow Equation (8) assuming the spiral dependence on t. The material information is now contained in $k_o$ and $\epsilon_o$. Aspnes et al. then expand the spiral dependence to first order in a growth increment $\Delta t$ to obtain the complex dielectric constant of that growth increment $$\epsilon_o = \langle\epsilon(t)\rangle - \frac{\Delta\langle\epsilon(t)\rangle}{2ik_o\Delta t}, \quad (9)$$

which is the dielectric function of the film. In this equation, $\langle\epsilon(t)\rangle$ is the ellipsometrically measured pseudo-dielectric function at some thickness t and $\Delta\langle\epsilon(t)\rangle/\Delta t$ is its differential (derivative) over $\Delta t$. Because of the dependence of $k_o$ on $\epsilon_o$, Equation (9) is a cubic equation in $\epsilon_o$ which can be solved for the value of $\epsilon_o$. However, in the earlier reported work, the computer system 42 used a linear approximation of Equation (9) for $\epsilon_o$. The computer system 42 then compares the measured dielectric constant of the thin film to a target value representing the desired composition and accordingly changes the Al valve 28. Further details of averaging periods, time constants, and other calculational procedures can be found in the patent.

Although the technique described above provides for vastly improved compositional control, it suffers some disadvantages. Its convergence to a final compositional value is felt to be too slow. Its convergence is controlled within a model assuming a homogeneous film, which is of course incorrect insofar as any correction is required. More generally, situations exist where the three-phase model is totally inappropriate. For structures having a very thin buried layer, that is, one that is not optically thick, the three-phase model is incorrect for a later grown layer. Furthermore, it may be desirable to compositionally grade an interface or an entire layer, for example, a quantum-well structure having a parabolically shaped potential well.

Theoretically, equations similar to those above could be numerically integrated with experimentally determined data as the structure is being grown. In fact, this is the standard approach for analyzing optical data taken on depositing thin films. However, false-data calculations show that when such analyses are done for thickness increments as small as those required for real time control, round-off errors, to say nothing about experimental noise, create mathematical instabilities that doom this approach.

SUMMARY OF THE INVENTION

The invention may be summarized as a method and apparatus for accurately deriving material information by ellipsometry on growing or etching films, where the composition may be a function of thickness, including a continuously varying function of thickness. Ellipsometry produces a sequence of pairs of data as the film is being grown or etched. An expression is used which is a derivative of ellipsometric data with respect to the thickness of a homogeneous film within a model, and the expression is exact within first order of the film thickness. The expression contains parameters, for example, dielectric constants, which physically characterize both the topmost film and the underlying material. Ellipsometric data are substituted for the parameters of the underlying material, the ellipsometric data being the pseudo-dielectric function in the above example, and the expression is then solved for the parameter characterizing the topmost film. Such a derived material parameter can be used to control the film growth in a feedback loop.

BRIEF DESCRIPTION OF THE DRAWING

The sole FIGURE.

BRIEF DESCRIPTION OF THE PREFERRED EMBODIMENT

Figure 1:
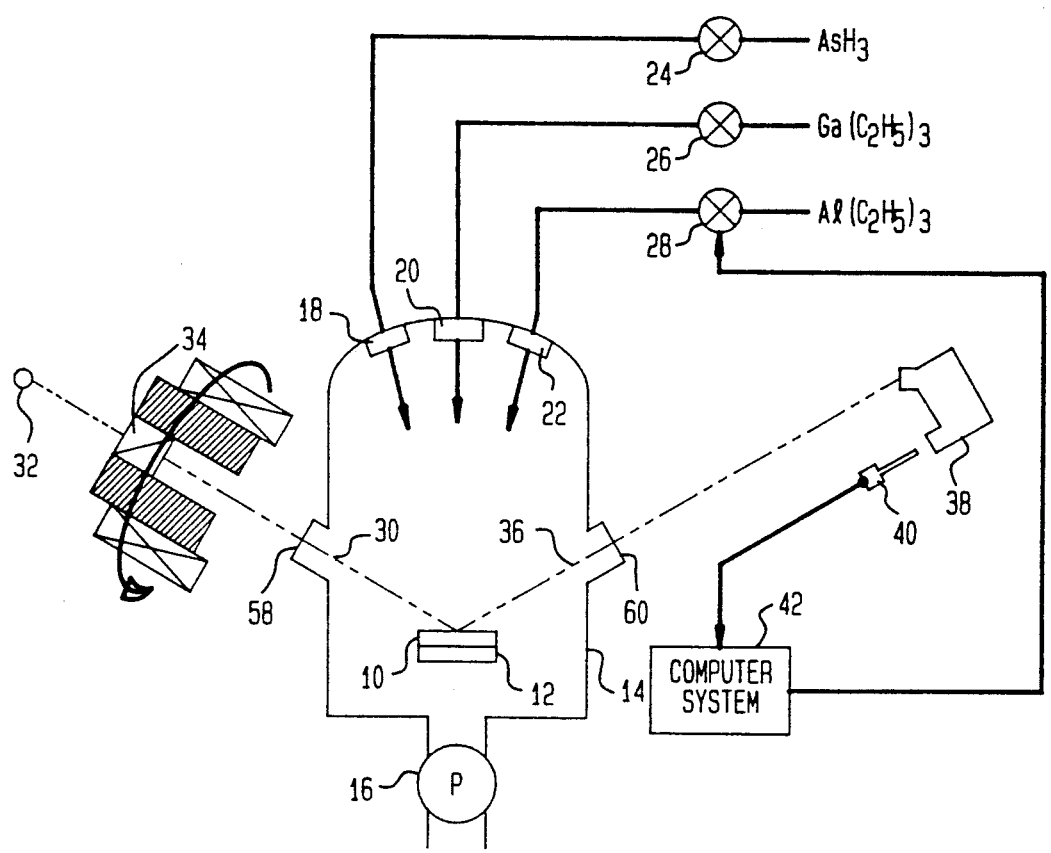
FIG. 1, is a schematic representation of an ellipsometrically controlled thin-film growth system.

I have published an expression for the pseudo-dielectric constant in a three-phase model $$\langle\epsilon\rangle = \epsilon_s + \frac{i4\pi t}{\lambda}\frac{\epsilon(\epsilon_s - \epsilon_o)(\epsilon_o - \epsilon_a)}{(\epsilon_s - \epsilon_a)\epsilon_o}(\epsilon_s - \epsilon_a\sin^2\phi)^{\frac{1}{2}}, \quad (10)$$

where $\epsilon_s$ is the complex dielectric constant of a homogeneous substrate, $\epsilon_o$ that of a homogeneous film of thickness t, and $\epsilon_a$ that of the ambient and equal to one for an air or vacuum ambient. Also, $\lambda$ is the wavelength of light, and $\phi$ is the angle of incidence and of reflection. As I explained in *Optical Properties of Solids: New Developments* ed. B. O. Seraphin (North Holland, 1976) on page 829, this equation is also derived within the three-phase model, but unlike Equation (8) it is a rigorous, not approximate, solution of this model that is accurate to first order in $t/\lambda$. Note that the first order expansion of Equation (8) for small t does not conform to Equation (10). Thus, Equation (10) is more accurate, but it still suffers from the conceptual problems of being based on a three-phase model, and it needs to be applied to a spatially varying structure for which the three-phase model does not apply. However, I have discovered that the growth increment $\Delta t$ can be considered to start from an interface at $t=0$ separating the growth increment from old material.

In this approach, the "substrate" dielectric function $\epsilon_s$ that appears in Equation (10) is simply replaced by the measured value of the pseudo-dielectric constant $\langle\epsilon\rangle$ prior to the deposition of the thickness increment $\Delta t$. The coefficient of t in Equation (10) is the derivative of the pseudo-dielectric function with respect to t, that is, $$\frac{d<\epsilon>}{dt} = \frac{i4\pi}{\lambda} \cdot \frac{\epsilon_s(\epsilon_s - \epsilon_o)(\epsilon_o - \epsilon_a)}{(\epsilon_s - \epsilon_a)\epsilon_o} (\epsilon_s - \epsilon_a\sin^2\phi)^{\frac{1}{2}}, \quad (11)$$

and this equation is exact within the three-phase model to first order in the film thickness t. The substitution of the pseudo-dielectric function $<\epsilon>$ for $\epsilon_s$ produces a complex equation quadratic in $\epsilon_o$ $$\frac{d<\epsilon>}{dt} \epsilon_o = \quad (12)$$

$$\frac{4\pi i<\epsilon>(<\epsilon> - \epsilon_o)(\epsilon_o - \epsilon_a)(<\epsilon> - \epsilon_a\sin^2\phi)^{\frac{1}{2}}}{\lambda(<\epsilon> - \epsilon_a)},$$

where all other factors are measured or accurately known. The pseudo-dielectric function is taken from a suitable average of a number of ellipsometrically measured values, and its derivative is taken from an average of a number of differences of ellipsometrically measured values, divided by an independently determined growth rate. The quadratic equation can be then exactly solved for $\epsilon_o$ as $$\epsilon_o = \xi \pm (\xi^2 - <\epsilon>\epsilon_a)^{\frac{1}{2}}, \quad (13)$$

where $$\xi = \frac{<\epsilon> + \epsilon_a}{2} + \frac{i\lambda(<\epsilon> - \epsilon_a)}{8\pi<\epsilon>(<\epsilon> - \epsilon_a\sin^2\phi)^{\frac{1}{2}}} \cdot \frac{d<\epsilon>}{dt}. \quad (14)$$

The correct root in Equation (13) is usually the one closet to the dielectric function of the substrate. For thick films and films having nearly the same dielectric constant as the substrate, the positive solution of Equation (13) is usually the correct root. Since only an increment Δt between points is needed, in principle $\Delta_o$ can be determined with no more than two adjacent points.

The substitution of $<\epsilon>$ for $\epsilon_s$ requires a conceptual break from conventional thinking in which the solution for the dielectric function of the outermost layer is built from the accumulated solutions for the dielectric functions of previous layers. The use of Equation (11) followed by the substitution of $<\epsilon>$ for $\epsilon_s$ and expressing $\epsilon_o$ in terms of $<\epsilon>$ and $d<\epsilon>/dt$ is equivalent to ignoring sample history and solving for the wave back-reflected from the layer(s) under that layer which was deposited in the most recent time increment Δt. In effect, $\epsilon_s$ represents these back reflectances and the substitution of $<\epsilon>$ for $\epsilon_s$ is legitimate because back reflectance exists whether or not the layer is actually present. The single approximation made in the above derivation is the assumption that the back reflectances of p- and s-polarizations originate with the same effective $\epsilon_s$.

The details of the calculation of the measured composition and the feedback control of the composition may be found in the references to Aspnes et al., whose procedures are simply modified by the substitution of Equation (12) for Equation (9), which is Equation (22) in the Aspnes et al. patent. Furthermore, Equation (12) is solved by the quadratic formula of Equation (13), and the numerical solution is compared with the target dielectric constant $\epsilon_t$ to obtain the measured difference in alloying percentage εn, which is fed back to the growth system using appropriate time constants.

False-data calculations have been performed modeling epitaxial growth of multi-layer structures and using the data reduction of the invention. The calculations show that the errors in composition are in the range 0.01 to 0.05% using Equation (12) as compared to 1 to 2% using Equation (9).

Although the above embodiment has used the formalism of the dielectric constant and the pseudo-dielectric function, other formalisms for the representations of ellipsometric data and material characterization may be used with the invention. Also, the feedback control is not limited to control of a ternary composition. The invention may be used with more complex compositions and with the control of growth parameters other than composition. The ellipsometer and growth system may assume other forms than those described above.

The invention thus provides a significant improvement over the prior method of extracting compositional information from ellipsometrically derived data of a growing thin film. Nonetheless, the improvement does not significantly increase the complexity of calculation. Thereby, the quality of heterostructures can be improved because of the increased control of composition in their growth.

What is claimed is:

1. A method of extracting spatially varying material data for a material having its upper surface modified, comprising the steps of:
   while said material is being modified measuring a sequence of pairs of values of a type of ellipsometric data;
   obtaining an expression including a derivative with respect to an incremental thickness of said type of ellipsometric data exact to lowest order in said incremental thickness, said expression containing a first pair of a type of material data for an upper portion of said material and at least a second pair of said type of said material data for a lower portion of said material;
   substituting in said expression selected ones of said sequence for said derivative and for said second pair;
   solving said expression for said first pair; and
   associating said first pair with said upper portion of said material, thereby physically characterizing said upper portion.

2. A method as recited in claim 1, wherein said ellipsometric data comprise pseudo-dielectric functions and said material data comprise dielectric constants.

3. A method as recited in claim 2, wherein said expression is a quadratic equation with respect to one of said dielectric constants for said upper portion.

4. A method as recited in claim 1, further comparing said first pair with a pair of target values for said material and, in response to said comparing, readjusting a growth condition for depositing said material while said measuring step is continuing.

5. A method as recited in claim 1, wherein said ellipsometric data equals said material data within a three-phase model of said material being grown.

6. A method of characterizing a thin film on a substrate, comprising the steps of:
   measuring by ellipsometry a sequence of effective complex dielectric constants of said thin film and substrate;
   substituting selected ones of said sequence of effective dielectric constants for first dielectric constants in an expression including a derivative of said effective dielectric constant with respect to an incremental thickness of said thin film, said expression being exact to first order in said thickness and additionally containing a second dielectric constant physically characterizing an upper portion of said thin film and substrate, said first dielectric constants physically characterizing a lower portion of said thin film and substrate, said expression being quadratic with respect to said second dielectric constant;

solving said quadratic expression for said second dielectric constant, thereby physically characterizing said upper portion of said thin film.

7. A method as recited in claim 6, wherein said effective dielectric constants are dielectric constants with a two-phase model and said second dielectric constant is for a middle portion of a three-phase model.

8. A method as recited in claim 6, further comprising the steps of:

continuously depositing said thin film on said substrate while said measuring step is being performed;

comparing said solved second dielectric constant to a predetermined dielectric constant; and adjusting a condition of said depositing step in response to a result of said comparing step.

9. A method as recited in claim 6, further comprising the steps of:

continuously etching said thin film on said substrate while said measuring step is being performed;

comparing said solved second dielectric constant to a predetermined dielectric constant; and adjusting a condition of said etching step in response to a result of said comparing step.

10. An ellipsometric feedback system for use in conjunction with a growth system for growing a multicomponent thin film on a substrate, comprising:

an ellipsometer measuring a sequence of a type of ellipsometric data of said thin film being grown; and computing means for obtaining a composition of an upper portion of said thin film from said ellipsometric data, said computing means solving an expression including a derivative of said type of ellipsometric data with respect to an incremental thickness of said thin film, said expression being exact to first order in said thickness and having substituted a plurality of said type of said ellipsometric data for data physically characterizing a lower portion of said thin film.

11. A system as recited in claim 10, further comprising:

comparing means for comparing said obtained composition with a predetermined target composition of said thin film; and correcting means for taking an output of said comparing means and providing therefrom a corrected control signal to said growth system.

* * * * *

UNITED STATES PATENT AND TRADEMARK OFFICE
CERTIFICATE OF CORRECTION

PATENT NO. : 5,277,747

DATED : January 11, 1994

INVENTOR(S) : David E. Aspnes

It is certified that error appears in the above-identified patent and that said Letters Patent is hereby corrected as shown below:

Column 4, lines 45 and 46, "Developmentsed." should read --Developments, ed.--.
Column 5, line 36, "closet" should read --closest--;
line 67, "εn" should read --Δn--.

Signed and Sealed this

Second Day of August, 1994

Attest:

BRUCE LEHMAN

Attesting Officer     Commissioner of Patents and Trademarks